(12) United States Patent
Willis et al.

(10) Patent No.: US 7,285,596 B2
(45) Date of Patent: Oct. 23, 2007

(54) ANIONIC POLYMERIZATION DIINITIATOR AND PROCESS FOR PREPARING SAME

(75) Inventors: Carl L. Willis, Houston, TX (US); Daniel E. Goodwin, Katy, TX (US); Grant W. Haddix, Katy, TX (US); Pierre N. Tutunjian, Houston, TX (US); Joy P. Cocchiara, Houston, TX (US); Harvey E. Atwood, Kingwood, TX (US); Craig A. Stevens, Katy, TX (US)

(73) Assignee: Kraton Polymers U.S. LLC, Houston, TX (US)

( * ) Notice: Subject to any disclaimer, the term of this patent is extended or adjusted under 35 U.S.C. 154(b) by 0 days.

(21) Appl. No.: 10/947,011

(22) Filed: Sep. 22, 2004

(65) Prior Publication Data

US 2005/0101741 A1  May 12, 2005

Related U.S. Application Data

(60) Provisional application No. 60/505,670, filed on Sep. 24, 2003.

(51) Int. Cl.
    *C08F 25/02* (2006.01)
(52) U.S. Cl. .................................... 525/242
(58) Field of Classification Search ............. 525/242
    See application file for complete search history.

(56) References Cited

U.S. PATENT DOCUMENTS

| 3,734,973 | A | 5/1973 | Farrar |
| 5,166,277 | A | 11/1992 | Goodwin et al. |
| 5,405,911 | A | 4/1995 | Handlin, Jr. et al. |
| 5,554,696 | A | 9/1996 | Fayt et al. |
| 5,750,055 | A | 5/1998 | Van Der Steen et al. |
| 6,043,316 | A | 3/2000 | St. Clair |
| 6,217,798 | B1 | 4/2001 | Willis et al. |
| 6,242,537 | B1 | 6/2001 | Bening et al. |
| 6,242,538 | B1 | 6/2001 | Bening et al. |
| 6,391,981 | B1 | 5/2002 | Willis et al. |
| 6,455,651 | B1 | 9/2002 | Willis et al. |
| 6,462,143 | B1 | 10/2002 | Willis et al. |
| 6,613,858 | B1 | 9/2003 | Sasagawa |
| 2002/0198343 | A1 | 12/2002 | Willis et al. |

OTHER PUBLICATIONS

Yu et al., Difunctional Initiators Based on 1,3-Diisopropenylbenzene. 3. Synthesis of a Pure Dilithium Adduct and Its Use as Difunctional Anionic Polymerization Initiator, Macromolecules; (Article); 1996; 29(8); 2738-2745.*

Yu et al., Synthesis and Properties of Poly[isobornyl methacrylate (IBMA)-b-butadiene (BD)-b-IBMA] Copolymers: New Thermoplastic Elastomers of a Large Service Temperature Range, Yu, J. M.; Dubois, Ph.; Jerome, R. Macromolecules; (Article); 1996; 29(23); 7316-7322.*

Yu et al., Difunctional Initiators Based on 1,3-Diisopropenylbenzene. 2. Kinetics and Mechanism of the sec-Butyllithium/1,3-Diisopropenylbenzene ReactionSynthesis of a Pure Dilithium Adduct and Its Use as Difunctional Anionic Polymerization Initiator, Macromolecules; (Article); 1996; 29(8); 1753-1761.*

Y.S. Yu, Ph. Dubois, R. Jerome and Ph. Teyssie; Difunctional Initiator Based on 1,3-Diisopropenylbenzene. 2. Kinetics and Mechanism of the sec-Butyllithium/ 1,3-Diisopropenylbenzene Reaction, *Marcomolecules* 1996, 29, 1753-1761.

Willam G. Kofron and Leona M. Baclawski; A Convenient Method for Estimation of Alkyllithium Concentrations, *J. Org. Chem.*, vol. 41, No. 10, 1976, 1879-1880.

* cited by examiner

*Primary Examiner*—Thurman K. Page
*Assistant Examiner*—Chukwuma Nwaonicha
(74) *Attorney, Agent, or Firm*—Donna Blalock Holguin

(57) ABSTRACT

Disclosed is an anionic diinitiator prepared using a diisopropenyl benzene compound and an organo lithium compound having primary polymerization sites. The anionic diinitiators are prepared by admixing a diisopropenyl benzene compound with diethyl ether, ethylene, an organo lithium compound, and a solvent under reaction conditions sufficient to prepare a diinitiator having primary lithium alkyl reactive sites. The diinitiators are particularly useful in preparing block copolymers.

20 Claims, No Drawings

ANIONIC POLYMERIZATION DIINITIATOR AND PROCESS FOR PREPARING SAME

CROSS-REFERENCE TO RELATED APPLICATION

The present application claims priority from commonly assigned U.S. provisional patent application Ser. No. 60/505,670, filed Sep. 24, 2003, entitled Anionic Polymerization Diinitiator and Process for Preparing Same.

BACKGROUND OF THE INVENTION

1. Field of the Invention

The present invention relates to anionic polymerization diinitiators and a process for preparing same. The present invention particularly relates to such initiators that are useful for the production of vinyl aromatic block copolymers.

2. Background of the Art

The use of anionic initiators to prepare block copolymers is well known. In a synthetic method, an initiator compound is used to start the polymerization of one monomer. The reaction is allowed to proceed until all of the monomer is consumed resulting in a living homopolymer. To this living homopolymer is added a second monomer that is chemically different from the first. The living end of the first polymer serves as the site for continued polymerization, thereby incorporating the second monomer as a distinct block into the linear polymer. The block polymer so grown is living until terminated.

Termination converts the living end of the block copolymer into a non-propagating species, thereby rendering the polymer unreactive toward additional monomers. A polymer so terminated is commonly referred to as a diblock copolymer. Initiators are commonly monofunctional. That is they have only one site that can initiate polymerization so that, in effect, the initiator is at one end of the polymer chain that builds in a single direction, that direction being away from the initiator. Exemplary monoinitiators include, for example, sec-butyl lithium.

Preparing a polymer using a diinitiator can offer advantages over preparing a similar polymer using a monoinitiator. By using a diinitiator, the polymer can be grown in both directions at the same time, thereby reducing the polymerization time. But the use of such diinitiators can also be troublesome. For example, U.S. Pat. No. 3,734,973, to Farrar, describes the production of anionic polymerization diinitiators by reacting diisopropenylbenzene compounds with organo monolithium compounds and then carrying out anionic copolymerization of styrene and butadiene using the diinitiators.

Unfortunately, the chemistry involved in the reaction of the diisopropenylbenzene and the lithium alkyl is prone to suffer from a competing side reaction that forms oligomers of diisopropenylbenzene. The oligomers consume diisopropenylbenzene and this limits the yield of the dilithium initiator. In addition and perhaps more importantly, the oligomers have more than two lithium centers per molecule. If all of the lithium centers in the oligomers initiate polymerization, a nonlinear, star, or radial polymer will result. The branching in such star and radial polymers leads to an increase in the melt viscosity of the polymer. This is undesirable if the desired polymer is a linear, difunctional anionic polymer.

One possible solution to the problem of oligomers having multiple initiation sites is disclosed in U.S. Pat. No. 6,217,798 B1 to Willis, et al. Therein it is disclosed that combining the components in a particular order, carrying out the reaction within a narrow temperature range, and carrying out the reaction in the presence of the appropriate amount of diethyl ether provides the advantage of minimizing the oligomerization of the diisopropenyl-benzene.

While the diinitiators prepared according to U.S. Pat. No. 6,217,798 B1 are clearly superior to the prior art diinitiators, they are not trouble free and require both time and resources to produce. It would be desirable in the art of preparing diinitiators for use in anionic polymerization to develop diinitiators that are more stable, less nucleophilic and less basic, and to prepare diinitiators that have primary anionic polymerizations sites of substantially equal reactivity.

SUMMARY OF THE INVENTION

In one aspect, the present invention is an anionic polymerization diinitiator comprising a diinitiator prepared by admixing a diisopropenyl benzene compound with diethyl ether, ethylene, an organo lithium compound, and a solvent under reaction conditions sufficient to prepare a diinitiator having primary lithium alkyl reactive sites.

In another aspect, the present invention is an anionic polymerization diinitiator having the general formula:

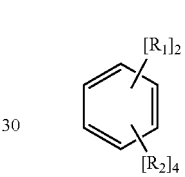

wherein $R_1$ has the general formula:

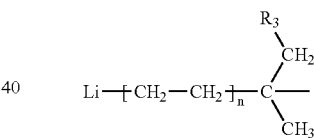

wherein $R_3$ is an aliphatic, cycloaliphatic, aromatic or alkyl-substituted aromatic hydrocarbon radical having from 1 to about 20 carbon atoms, each n is independently an integer having a value from 1 to 10, and $R_2$ is hydrogen or an alkyl or cycloalkyl radical containing from 1 to 6 carbon atoms.

In still another aspect, the present invention is a process for preparing a an anionic polymerization diinitiator comprising admixing a diisopropenyl benzene compound, diethyl ether, ethylene, an organo lithium compound, and a solvent under reaction conditions sufficient to prepare a diinitiator having primary lithium alkyl reactive sites.

Another aspect of the present invention is a block copolymer prepared using a diinitiator prepared by admixing a diisopropenyl benzene compound with diethyl ether, ethylene, an organo lithium compound and a solvent under reaction conditions sufficient to prepare a diinitiator having primary lithium alkyl reactive sites.

DETAILED DESCRIPTION OF THE PREFERRED EMBODIMENTS

In the practice of the method of the present invention, an anionic polymerization diinitiator is prepared by admixing a diisopropenyl benzene compound with diethyl ether and a solvent. The diisopropenyl benzene compounds useful with the present invention have a general formula:

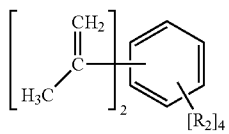

is wherein $R_2$ is hydrogen or an alkyl or cycloalkyl radical containing from 1 to 6 carbon atoms. Exemplary diisopropenyl benzene compounds include: 1,2-diisopropenylbenzene; 1,3-diisopropenylbenzene; 1,4-diisopropenylbenzene; 3,4,5,6-tetramethyl-1,2-diisopropenylbenzene; 2,4,5,6-tetraethyl-1,3-diiso-propenylbenzene; 2,3,5,6-tetra-n-hexyl-1,4-diisopropenyl-benzene; 3,4-dicyclohexyl-1,2-diisopropenyl-benzene; 5-(3-methyl-cyclopentyl)-1,3-diisopropenylbenzene; 3-cyclopentyl-methyl-6-n-propyl-1,4 -diisopropenyl-benzene; 4-(2-cyclo-butyl-1-ethyl))-1,2-diisopropenylbenzene; 3-(2-n-propylcyclopropyl)-1,4 -diisopropenylbenzene; 2-methyl-5-n-hexyl-1,3-diisopropenylbenzene; 4-methyl-1,2-diiso-propenyl-benzene; 5-ethyl-1,3-diisopropenylbenzene; 3-methyl-1,4-diisopropenylbenzene; and the like. 1,3-diisopropenylbenzene is preferred. Mixtures of diisopropenyl benzene compounds can also be used with the present invention.

The diinitiators of the present invention are prepared by contacting a dialkene intermediate with an organo alkali metal, preferably an organo lithium compound, in a suitable solvent at a temperature within the range from about 0° C. to about 150° C., preferably at a temperature within the range from about −25° C. to about 50° C. Particularly effective are organo lithium compounds having the general formula:

RLi wherein R is an aliphatic, cycloaliphatic, aromatic or alkyl-substituted aromatic hydrocarbon radical having from 1 to about 20 carbon atoms. Exemplary organo lithium compounds are isopropyllithium, sec-butyllithium, tert-octyllithium, tert-butyllithium, and the like. Sec-butyl and tert-butyllithium are preferred for use with the present invention. Mixtures of organo lithium compounds can also be used with the method of the present invention.

Suitable solvents for use with the method of the present invention include straight and branched chain hydrocarbons such as pentane, hexane, heptane, octane and the like, as well as alkyl-substituted derivatives thereof; cycloaliphatic hydrocarbons such as cyclopentane, cyclohexane, cycloheptane and the like, as well as alkyl-substituted derivatives thereof; aromatic and alkyl-substituted derivatives thereof; aromatic and alkyl-substituted aromatic hydrocarbons such as benzene, naphthalene, toluene, xylene and the like; hydrogenated aromatic hydrocarbons such as tetralin, decalin and the like; linear and cyclic ethers such as dimethyl ether, methylethyl ether, diethyl ether, 1,3-diethoxypropane, tetrahydrofuran and the like. In the practice of the present invention, the solvent is preferably cyclohexane. Mixtures of solvents can also be used.

In the practice of the present invention, the process for preparing the diinitiators goes through an intermediate compound, the compound having a general formula:

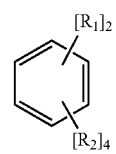

wherein $R_2$ is hydrogen or an alkyl or cycloalkyl radical containing from 1 to 6 carbon atoms, and $R_4$ has the general formula:

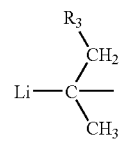

wherein $R_3$ is as defined hereinbefore. It is the tertiary reaction site on $R_4$ that is further reacted with ethylene to make it a primary anion polymerization site and thereby more removed from the aromatic ring. While not wishing to bound by any theory, it is believed that, with the present invention, moving the polymerization site away from the aromatic ring reduces the electronic interaction between the polymerization sites. It was observed that tertiary polymerization sites such as those on the intermediate compound tended to be of unequal reactivity wherein chain propagation would tend to occur unevenly. Stated another way, the chain propagation occurred to a greater extent on one of the polymerization sites of the tertiary lithium diinitiators. It has been observed with the diinitiators of the present invention that chain propagation occurs substantially equally at both polymerization sites.

The organo lithium diinitiators of the present invention have primary anion polymerization sites. This is an advantage over the conventional diinitiators that have tertiary anion polymerization sites in that the diinitiators of the present invention are more thermally stable. Primary carbon anions are much less basic and less nucleophilic than tertiary carbon anions. For these reasons, diinitiators having primary carbon anion functionality are less prone to abstracting protons from solvent or monomers. The avoidance of these side reactions leads to improved storage stability and improved stability in the presence of monomer. This improved thermal stability increases the shelf life of the diinitiators allowing them to be stored and even shipped permitting diinitiator production to be centralized. Such centralization often leads to reductions in cost and an increase in quality allowing for an improvement in the polymers produced therewith. In a like manner, the primary carbon anion diinitiators are preferred for the polymerization of monomers like acrylics that are sensitive to side reactions involving nucleophilic substitution.

Following the reaction at the tertiary site, the final diinitiator has the general formula:

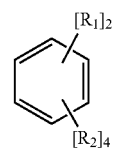

wherein $R_1$ has the general formula:

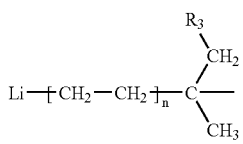

wherein $R_3$ is an aliphatic, cycloaliphatic, aromatic or alkyl-substituted aromatic hydrocarbon radical having from 1 to about 20 carbon atoms. Preferably $R_3$ is an alkyl or cycloalkyl radical having from 1 to 6 carbon atoms, preferably 2 to 4 carbon atoms, with 4 carbon atoms being the most preferred. Each n in the diinitiator is independently an integer having a value from 1 to 10, preferably from 1 to 5 and even more preferably n is 1. Those of ordinary skill in the art will recognize that in certain instances, the value of each n will be the same in the diinitiator while in other instances, the values will differ. $R_2$ is hydrogen or an alkyl or cycloalkyl radical containing from 1 to 6 carbon atoms. In the more preferred embodiment, $R_2$ is hydrogen.

Although any of the diisopropenyl benzene compounds described before can be used to prepare the diinitiators of the present invention, the preferred diisopropenyl benzene compound is 1,3-diisopropenyl benzene. Similarly, any of the organo lithium compounds described before can be used with the present invention, but preferably the organo lithium compounds used to prepare the diinitiators of the present invention is sec-butyl lithium. Consequentially, a more preferred diinitiator of the present invention has the general structure:

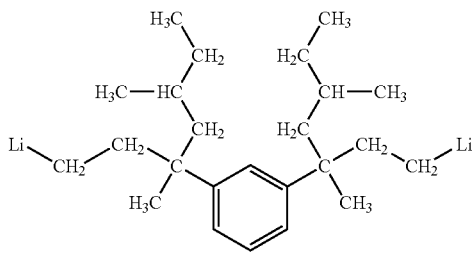

wherein the diinitiator is prepared using diisopropenyl benzene and sec-butyl lithium.

In a further preferred embodiment, the dilithium initiators of the present invention are prepared by reacting a lithium alkyl compound with a diisopropenylbenzene compound at a mole ratio of diisopropenylbenzene to lithium alkyl in the range of from about 0.4:1 to about 0.6:1, preferably from about 0.45:1 to about 0.55:1, and most preferably about 0.5:1. Diethyl ether is utilized in the reaction at a molar ratio of diethyl ether to lithium alkyl compound of from about 0.1:1 to about 1.5:1 for secondary lithium alkyls and about 2:1 for tertiary lithium alkyls, preferably from about 0.4:1 to about 1.1:1, and most preferably about 1:1 for secondary lithium alkyls and about 2:1 for tertiary lithium alkyls. Ethylene can be used in excess and is preferably used at a mole ratio of ethylene to lithium alkyl of from about 1:1 to about 10:1, preferably from about 2:1 to about 9:1 and most preferably from about 5:1 to about 8:1. Therefore, another preferred embodiment of the present invention is a diinitiator having the general formula:

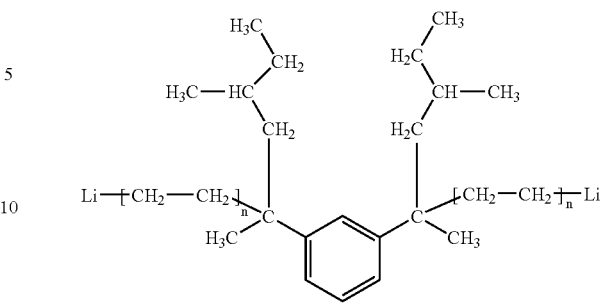

wherein each n is independently an integer having a value of from 1 to 10, preferably from 1 to 5.

The method of the present invention can be performed by first admixing a diisopropenyl benzene compound with diethyl ether and a solvent, and then with an organo lithium compound followed by addition of ethylene to the admixture. In an alternative embodiment, the method of the present invention is performed by first admixing diisopropenyl benzene compound with diethyl ether, ethylene and a solvent, and then with an organo lithium compound. The components used with the method of the present invention can be admixed in any order known to be useful to those of ordinary skill in the art of preparing anionic polymerization diinitiators.

In another embodiment, the present invention is a block copolymer prepared using a diinitiator prepared by admixing a diisopropenyl benzene compound with diethyl ether, ethylene, an organo lithium compound and a solvent under reaction conditions sufficient to prepare a diinitiator having primary lithium alkyl reactive sites. The block copolymers of the present invention are preferably linear. The linear polymers typically have a general formula ABA or BAB-BAB. In this general formula, A is a thermoplastic polymer block selected from vinyl aromatic polymer blocks, conjugated cyclic diene polymer blocks and acrylic polymer blocks having a Tg>25° C.; and B is an elastomeric polymer block selected from conjugated acyclic diene polymer blocks, optionally hydrogenated, and acrylic polymer blocks with a Tg<25° C. The total average molecular weight of the block copolymer of the present invention is preferably within the range of from about 2,000 to about 300,000 daltons. More preferably, the number average molecular weight is from about 3,000 to about 250,000 daltons, and most preferably, from about 30,000 to 250,000 daltons.

The block copolymers of the present invention may have a tapered block structure. Each block should contain predominantly only one component, A or B. The presence of the other component than the predominant one should be less than 50 weight percent, more preferably less than 30 weight percent. Most preferably each block contains only one or essentially only one component, i.e., A or B.

Suitable vinyl aromatic compounds useful with the process of the present invention include those having from 8 to 20 carbon atoms and include styrene, o-methylstyrene, p-methylstyrene, p-tert-butylstyrene, 2,4-dimethylstyrene, α-methylstyrene, vinylnaphthalene, vinyltoluene, vinylxylene, 1,1-diphenylethylene, and mixtures thereof. Preferred monovinyl aromatic compounds are styrene, alpha-methylstyrene and para-methylstyrene, styrene being the most preferred. For the purposes of the present invention, a styrenic block copolymer is any block copolymer polymer prepared with a suitable vinyl aromatic compound.

Suitable acrylic compounds for use with the present invention include alkyl methacrylates wherein the alkyl group has up to 14 carbon atoms inclusive. Illustrative of such methacrylate esters are methyl methacrylate, ethyl methacrylate, sec-butyl methacrylate, t-butyl methacrylate, i-amyl methacrylate, hexyl methacrylate, decyl methacrylate and dodecyl methacrylate. The preferred alkyl methacrylates are branched-butyl methacrylates, i.e., iso-butyl methacrylate and t-butyl methacrylate. The desired poly(alkyl methacrylate) block is produced by directly polymerizing the corresponding alkyl methacrylate monomer or alternatively the desired block is obtained by polymerizing a more easily polymerizable methacrylate and subsequently transesterifying the product to introduce the desired alkyl group.

Conjugated dienes suitable for use with the present invention include those having from 4 to 8 carbon atoms, for example 1,3-butadiene 2-methyl-1,3-butadiene (isoprene), 2,3-dimethyl-1,3-butadiene, 1,3-pentadiene, 1,3-hexadiene and 1,3-cyclohexadiene. Mixture of such dienes may also be used. Preferred conjugated dienes are 1,3-butadiene and isoprene.

The polymers of the present invention have many uses including such end uses as: bitumen additives for road and roofing; sealants, adhesives, and the like. Additionally, these polymers may be used in compounds with polyolefins like polypropylene or polyethylene. Such compounds would find utility in personal hygiene, footwear, films, and automotive applications. The polymers of the present invention may also, optionally, contain various additives, such as antioxidants, ultraviolet absorbers, light stabilizers, flow promoters, lubricants, or coloring agents. Preferably the amount of these additives present in the polymer composition is not more than 5 weight parts per 100 weight parts of block copolymer. The polymers of the present invention can be used in applications where they are filled with talc, carbon black, or various silicates.

EXAMPLES

The following example is provided to illustrate the present invention. The example is not intended to limit the scope of the present invention and it should not be so interpreted. Amounts are in weight parts or weight percentages unless otherwise indicated.

Example 1

An anionic polymerization diinitiator having primary (1°) anionic centers was prepared by charging, under nitrogen, 8.17 grams (g) (0.05 mol) 1,3-diisopropenylbenzene (1,3-DIPB), 22 g (0.79 mol) ethylene, 200 g diethyl ether, and 1700 g cyclohexane into a 1 gallon (3.78 L) autoclave and bringing the admixture to 30° C. Over a period of 210 minutes, 57.5 g of an 11.9% wt solution of sec-butyllithium (s-BuLi) (0.10 mol) was added to the autoclave. The temperature of the reaction was controlled at less than 30° C. The initially formed red color of the reaction mixture changed to a light yellow hue with time. This was an indication that the initially formed 3° benzylic anions (from the addition of s-BuLi to the C=C centers in the 1,3-DIPB) which gave a deep red colored solution was reacting with ethylene to form the desired 10 anionic centers which afforded a light yellow colored solution. To confirm this observation, an aliquot of the lithium alkyl solution was terminated by the addition of an excess of $D_2O$. This treatment effectively replaced all of the C—Li centers in the terminated sample with C-D moieties. Analysis of the deuterated adduct by a $C^{13}$ NMR method found an abundance of —$CH_2D$ centers; such functionality would have been anticipated from reaction of the desired primary alkyl lithium product species, —$CH_2Li$, with the $D_2O$ quenching agent. There was no signal for a $D_2O$ quenched —CR2Li center which would have been expected had the addition of ethylene to the initially formed s-BuLi+1,3-DIPB adduct been less than quantitatively ethylated. Analysis of the integrated $C^{13}$ NMR spectrum found over 0.85 —$CH_2D$ centers for every s-Bu group that had added to 1,3-DIPB. It was concluded that over 85% of the C—Li centers that were formed as a result of the addition of the s-BuLi reagent to 1,3-DIPB were of the desired 1° alkyl anion type prior to quenching the sample. The $D_2O$ quenched sample was further characterized using a gas chromatography-mass spectroscopy (GC-MS) technique. The results of this test corroborated the earlier findings. The principal product in the reaction mixture was the di-deuterated molecule that arose from quenching the desired diinitiator having 1° anionic centers. The structure of the product prior to $D_2O$ quenching was:

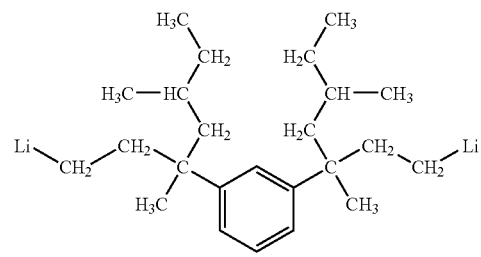

The remainder of the new diinitiator solution was reserved for polymerization studies.

Example 2

The procedure of Example 1 was repeated with essentially the same results. When the preparation of the new diinitiator was complete, 200 g of butadiene was added to the reactor and polymerization ensued. The polymerization temperature was controlled below 50° C. When polymerization was complete, an aliquot of the living anionic polymer was removed from the reactor and terminated by the addition of MeOH. Analysis of the product polymer using a proton nuclear magnetic resonance, H-NMR, technique found polybutadiene having a number average molecular weight ($M_N$) of 4,200 ($M_N$(theory)=4,000) which was in good agreement with the theoretical value based upon the amount of initiator and monomer that were used in the experiment. Over 41% of the polymer had been formed by 1,2-addition of the butadiene to the growing anionic polymer chain. Further analysis of this sample using a gel permeation chromatography, GPC, technique, found a monomodal molecular weight distribution of polybutadiene species which was consistent with effective initiation of polymerization with the new diinitiator.

The remainder of the living polybutadiene solution was treated with an excess of ethylene oxide. Analysis of the ethylene oxide capped polybutadiene using a $C^{13}$ NMR method found 2 hydroxyl end groups for every 1,3-DIPB residue in the polybutadiene. In essence, a quantitative yield of a telechelic polybutadiene diol was realized using the new anionic polymerization diinitiator having primary (1°) anionic centers.

9

Example 3

The product of Example 1, an anionic polymerization diinitiator having primary (1°) carbon anion centers, was prepared using a different order of addition of the reactive reagents. In this experiment, 372 g of an 8.6% wt solution of s-BuLi (0.5mol) was placed in the reactor under nitrogen. About 20 g (0.71 mol) ethylene was added to the reaction vessel. Over a period of 40 minutes, a solution of 39.6 g (0.25 mol) 1,3-DIPB in a solvent composed of 290 g cyclohexane and 78 g diethyl ether was added to the reactor. The temperature of the reaction mixture was controlled at less than 30° C. Reaction was allowed to proceed for 1 hr. An aliquot of the reaction product was analyzed for active C—Li species using a titration method that employed diphenylacetic acid as the titrant (Kofron, W. G., and Baclawski, Leona; *A Convenient Method for Estimation of Alkyllithium Concentrations*, Journal of Organic Chemistry, 41(10), 1879–80.); this analysis found the C—Li concentration to be 0.49 mol/l of solution. Over 97% of the C—Li activity in the reactant S-BuLi reagent was preserved in the new lithium alkyl product. An aliquot of the new lithium alkyl solution was analyzed by an H-NMR, technique. The presence of the desired primary alkyl lithium center, —CH2Li, in this product was detected directly by a broad signal at −0.5 to −2.5 ppm which was due to the two hydrogen atoms on the carbon center bearing the C—Li bond. Analysis of the integrated H-NMR spectrum found 1.97 —CH2Li moieties per 1,3-DIPB center in the new lithium alkyl reagent. This demonstrated that a near quantitative yield of the lithium reagent, as described in Example 1, was realized. The remainder of the new anionic polymerization diinitiator having primary (1°) carbon anion centers was reserved for anionic polymerization studies.

Example 4

The procedure of Example 3 was modified to add the ethylene reagent after the s-BuLi+1,3-DIPB adduct had been formed. In addition, a substantial excess of ethylene was used which resulted in oligomerization of ethylene onto the living end of the initially formed diinitiator having primary (1°) anionic centers.

In this experiment, 313 g of a 10.2% wt solution of s-BuLi (0.5 mol) was placed in the reactor under nitrogen. Over a period of 10 minutes, a solution of 39.6 g (0.25 mol) 1,3-DIPB in a solvent composed of 349 g cyclohexane and 78 g diethyl ether was added to the reactor. The temperature of the reaction mixture was controlled at less than 55° C. Ethylene (38.1 g (1.36 mol)) was then added to the reactor. After 3.5 hr, an aliquot of the reaction product was tested using the titration method of Kofron. The C—Li activity of the solution was assayed to be 0.46 mol/l which corresponded to a yield of 92% basis the amount of s-BuLi used in the preparation. As had been observed in Example 3, H-NMR analysis of this found that essentially all of the C—Li centers in the initially formed s-BuLi+1,3-DIPB adduct had been ethylated to form primary carbon anion centers. A sample of the new dilithium alkyl reagent was terminated by the addition of MeOH and analyzed using the GC-MS procedure described in Example 1. A mixture of species were found which were separated in molecular weight by a mass of 28. Molecules resulting from the addition of 2, 3 and 4 ethylene units were identified; higher oligomers likely were present in the mixture as well but could readily characterized. The new anionic polymerization diinitiator having primary (1°) anionic centers could be characterized a mixture of species having the following general structure:

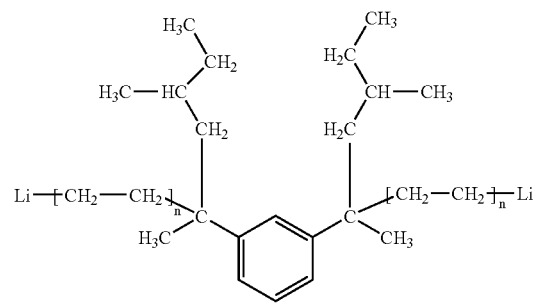

wherein each n is independently an integer.

The remainder of the solution was reserved for anionic polymerization experiments.

What is claimed is:

1. An anionic polymerization diinitiator prepared by admixing a diisopropenyl benzene compound selected from the group 1,2-diisopropenylbenzene; 1,3-diisopropenylbenzene; 1,4-diisopropenylbenzene; 3,4,5,6 - tetramethyl-1,2-diisopropnenylbenzene; 2,4,5,6-tetraethyl-1,3-diiso-propenylbenzene; 2,3,5,6-tetra-n-hexyl-1,4-diisopropenyl-benzene; 3,4-dicyclohexyl-1,2-diisopropenyl-benezene; 5-(3-methyl-cyclopentyl)-1,3-diiso-propenylbenzene; 3-cyclopentyl-methyl-6-n-propyl-1,4 -diisopropenyl-benzene; 4-(2-cyclo-butyl-1-ethyl)-1,2-diisopropenylbenzene; 3-(2-n-propylcyclopropyl)-1,4-diisopropenylbenzene; 2-methyl-5 -n-hexyl-1,3-diisopropenylbenzene; 4-methyl-1,2-di-iso-propenyl-benzene; 5-ethyl-1,3-diisopropenylbenzene; 3-methyl-1,4-diisopropenylbenzene; and mixtures thereof, with diethyl ether, ethylene, an organo lithium compound, and a solvent under reaction conditions sufficient to prepare a diinitiator having primary lithium alkyl reactive sites.

2. The anionic polymerization diinitiator of claim 1 wherein the diisopropenyl benzene compound is 1,3-diisopropenylbenzene.

3. The anionic polymerization diinitiator of claim 1 wherein the organo lithium compound is selected from the group isopropyllithium, sec-butyllithium, tert-octyllithium, tert-butyllithium, and mixtures thereof.

4. The anionic polymerization diinitiator of claim 3 wherein the organo lithium compound is sec-butyl lithium.

5. The anionic polymerization diinitiator of claim 1 wherein the solvent is selected from the group cyclopentane, cyclohexane, hexane, cycloheptane, heptane, benzene, naphthalene, toluene, xylene, tetralin, decalin, dimethyl ether, methylethyl ether, diethyl ether, 1,3-diethoxypropane, tetrahydrofuran and mixtures thereof.

6. The anionic polymerization diinitiator of claim 5 wherein the solvent is cyclohexane.

7. An anionic polymerization diinitiator having the general formula:

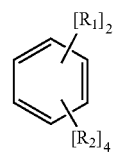

wherein R₁ has the general formula:

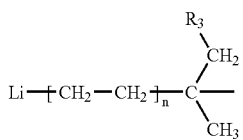

and R₃ is an aliphatic, cycloaliphatic, aromatic or alkyl-substituted aromatic hydrocarbon radical having from 1 to about 20 carbon atoms, each n is independently an integer having a value from 1 to 10, and R₂ is hydrogen or an alkyl or cycloalkyl radical containing from 1 to 6 carbon atoms.

8. The anionic polymerization diinitiator of claim 7 wherein ₃ is an alkyl or cycloalkyl radical containing from 1 to 6 carbon atoms.

9. The anionic polymerization diinitiator of claim 8 having the general formula:

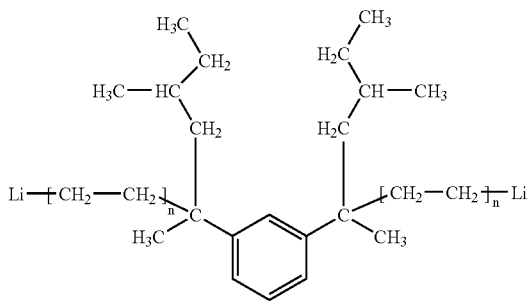

wherein each n is independently an integer having a value of from 1 to 10.

10. A process for preparing an anionic polymerization diinitiator comprising admixing a diisopropenyl benzene compound, diethyl ether, ethylene, an organo lithium compound, and a solvent under reaction conditions sufficient to prepare a diinitiator having primary lithium alkyl reactive sites.

11. The process of claim 10 wherein the diisopropenyl benzene compound is 1,3-diisopropenylbenzene; the organo lithium compound is sec-butyl lithium, and the solvent is cyclohexane.

12. The process of claim 11 wherein the mole ratio of 1,3-diisopropenylbenzene to sec-butyl lithium is from about 0.4:1 to about 0.6:1.

13. The process of claim 12 wherein the mole ratio of 1,3-diisopropenylbenzene to sec-butyl lithium is from about 0.45:1 to about 0.5 5:1.

14. The process of claim 13 wherein the mole ratio of 1,3-diisopropenylbenzene to sec-butyl lithium is about 1:2.

15. The process of claim 11 wherein the molar ratio of diethyl ether to sec-butyl lithium is from about 0.1:1 to about 2:1.

16. The process of claim 15 wherein the molar ratio of diethyl ether to sec-butyl lithium is about 1:1.

17. The process of claim 11 wherein the mole ratio of ethylene to sec-butyl lithium is from about 1:1 to about 10:1.

18. The process of claim 17 wherein the mole ratio of ethylene to sec-butyl lithium is from about 2:1 to about 9:1.

19. The process of claim 18 wherein the mole ratio of ethylene to sec-butyl lithium is from about 5:1 to 8:1.

20. An anionic polymer prepared using the diinitiator of claim 1.

* * * * *

UNITED STATES PATENT AND TRADEMARK OFFICE
CERTIFICATE OF CORRECTION

| | |
|---|---|
| PATENT NO. | : 7,285,596 B2 |
| APPLICATION NO. | : 10/947011 |
| DATED | : October 23, 2007 |
| INVENTOR(S) | : Carl L. Willis et al. |

It is certified that error appears in the above-identified patent and that said Letters Patent is hereby corrected as shown below:

Col. 11
Claim 8, line 17 after "wherein" insert --R-- before "3".

Col. 12
Claim 13, line 16, delete "0.5 5" and insert --0.55--.

Signed and Sealed this

Eighteenth Day of December, 2007

JON W. DUDAS
*Director of the United States Patent and Trademark Office*